United States Patent [19]

Zamora

[11] Patent Number: 5,738,838
[45] Date of Patent: Apr. 14, 1998

[54] IKVAV PEPTIDE RADIOPHARMACEUTICAL APPLICATIONS

[75] Inventor: Paul O. Zamora, Albuquerque, N. Mex.

[73] Assignee: Rhomed Incorporated, Albuquerque, N. Mex.

[21] Appl. No.: 998,820

[22] Filed: Dec. 30, 1992

Related U.S. Application Data

[63] Continuation-in-part of Ser. No. 840,077, Feb. 20, 1992, Pat. No. 5,443,816.

[51] Int. Cl.$^6$ .................. A61K 49/00; G01N 33/15
[52] U.S. Cl. .................. 424/9.341; 424/1.69; 424/9.1; 424/1.11; 424/9.3; 530/300; 530/326; 530/330; 534/10; 534/14; 534/15
[58] Field of Search .................. 424/1.53, 9.341, 424/1.11, 1.69, 9.1, 9.3, 9.34, 9.4; 530/402, 391.5, 300, 326, 330; 534/14, 10, 15

[56] References Cited

U.S. PATENT DOCUMENTS

| | | | |
|---|---|---|---|
| 4,427,646 | 1/1984 | Olexa et al. | 424/1.1 |
| 4,479,930 | 10/1984 | Hnatowich | 424/1.1 |
| 4,668,503 | 5/1987 | Hnatowich | 424/1.1 |
| 4,732,864 | 3/1988 | Tolman | 436/547 |
| 4,877,868 | 10/1989 | Reno et al. | 530/390 |
| 4,986,979 | 1/1991 | Morgan, Jr. et al. | 424/1.1 |
| 5,330,911 | 7/1994 | Hubbell et al. | 530/330 |
| 5,346,687 | 9/1994 | Rhodes | 424/1.49 |
| 5,371,184 | 12/1994 | Rajagopalan et al. | 530/324 |
| 5,443,816 | 8/1995 | Zamora et al. | 424/1.69 |
| 5,460,785 | 10/1995 | Rhodes et al. | 424/1.49 |

FOREIGN PATENT DOCUMENTS

| | | | |
|---|---|---|---|
| 2016235 | 11/1990 | Canada . | |
| 0196669 | 4/1986 | European Pat. Off. | C07K 17/06 |
| 0210684 | 7/1986 | European Pat. Off. | A61K 49/02 |
| 0250013 | 5/1987 | European Pat. Off. | C07F 13/00 |
| 0359347 | 8/1989 | European Pat. Off. | A61K 47/00 |
| 2 225 579 | 6/1990 | United Kingdom . | |
| WO 91/01144 | 2/1991 | WIPO . | |
| WO92/13572 | 2/1992 | WIPO | A61K 49/02 |

OTHER PUBLICATIONS

Anger, K. "Radionuclide Studies of the Lung" Sperber, editor, *Radiologic Diagnosis of Chest Disease*, Springer-Verlag, New York pp. 140–153 (1990).
Clement, B, "Hepatocyte Attachment to Laminin Is Mediated Through Multiple Receptors", *J. of Cell Biology*, vol. 110, pp. 185–192 (1990).
Hynes, R.O., "Integrins: Versatility, Modulation, and Signalling in Cell Adhesion", *Cell.* vol. 69, pp. 11–25 (1992).
Kleinman, H.K., "Identification of a 110–kDa Nonintegrin Cell Surface Laminin–Binding Protein Which Recognizes an A Chain Neurite–Promoting Peptide", *Archives of Biochem.* vol. 290 No. 2, pp. 320–325 (1991).

Kanemoto, T., et al., "Identification of an Amino Acid Sequence from the Laminin A Chain that Stimulates Metastasis and Collagenase IV Production", *Proc. Nat. Acad. Sci. (USA)*, vol. 87 pp. 2279–2283 (1990).
Miller, R.F., et al., "Pulmonary Nuclear Medicine", *Eur. J. Nucl. Med.*, vol. 19, pp. 355–368 (1992).
Nomizu, M., et al., "The All–D–Configuration Segment Containing the IKVAV Sequence of Laminin A. Chain has Similar Activities fo the All–L–Peptide In Vitro and In Vivo", *J. Biol. Chem.*, vol. 267, pp. 14188–14121 (1992).
Sephel, G.C., "Laminin A Chain Synthetic Peptide Which Supports Neurite Outgrowth", *Biochem. Biophys. Res. Comm.*, vol. 162, pp. 821–829 (1989).
Skubitz, A.P., "Synthetic peptides from the Carbosy–terminal Globular Domain of the A Chainof Laminin: Their Ability to Promote Cell Adhesion and Neurite Outgrowth, and Interact with Peparin and the Beta1 Integrin Subunit", *J. Cell Biol.*, vol. 115, pp. 1137–1148 (1991).
Tashiro, Ken–Ichiro, et al., "A Synthetic Peptide Containing the IKVAV Sequence from the Chain of Laminin Mediates Cell Attachment, Migration, and Neurite Outgrowth", *J. Biol. Chem.*, vol. 27, pp. 16174–16182 (1989).
Tetalman, M.R., et al., "Perfusion Scans in Normal Volunteers", *Radiology*, vol. 106, pp. 593–594 (1973).
Thompson, H.L., et al., "Mast Cells Chemotax to Laminin with Enhancement After IgE–Mediated Activation", *J. Immunol.*, vol. 143, pp. 4188–4192 (1989).
Thompson, H.L., et al., "Identification of an Amino Acid Sequence in the Laminin A Chain Mediating Mast Cell Attachment and Spreading", *Immunology*, vol. 72, pp. 144–149 (1991).
Webber, M.M., et al., "Variants of the Normal Lung Scan: Correlation with Pulmonary Function Tests", *J. Nucl. Med.*, vol. 13, p. 476 (1972).
Yamada, K.M., et al., "Adhesive Recognition Sequences", *J. Biol. Chem.*, vol. 266, pp. 2809–2812 (1992).
Pimm, M.V., et al., "In labelling of a branched polypeptide drug carrier with a poly (L–lysine–backbone," Int'l J. Pharm., vol. 79, pp. 77–80 (1992).
Zamora, P.O., et al., Lung Uptake of 99mTc–Laminin Peptide PA22–2 Is Decreased in Emphysema and Increased in Tumored Lung, Abstract, J. Nucl. Med., vol. 34, No. 5, (1993), Abstract No. 1133.
Zamora, P.O, et al., Biological distribution of 99mTc–labeled.

(List continued on next page.)

*Primary Examiner*—John Kight
*Assistant Examiner*—D. L. Jones
*Attorney, Agent, or Firm*—Darby & Darby

[57] ABSTRACT

Peptides useful for lung imaging, and preferably containing a biological-function domain which includes the sequence Ile-Lys-Val-Ala-Val (IKVAV) (SEQ. ID NO. 1) and a medically useful metal ion-binding domain are labeled with medically useful metal ions for use in a variety of diseases and pathologic conditions, and particularly diagnostic imaging of diseases and pathologic conditions of the lung.

16 Claims, No Drawings

OTHER PUBLICATIONS

Yigsr and IKVAV laminin peptides in rodents: 99mTc–IKVAV peptide localizes to the lung, Biochemica et Biophysica Acta, vol. 1182, No. 2 (1993), p. 197–204.

Sandrock, B., "Kinetics of I.V. Injected 1-131-Labeled Laminin–$C_1$–Fragmen in Normal and Tumor–Bearing Nude Mice," Proceedingsof the AACR, vol. 30, Abstract No. 390 (1989).

Liotta, Lance A., Laminin Receptors on Human Breast Carcinoma: Role in. Invasion of the Extracellular Matrix, Understanding Breast Cancer: Clinical and Laboratory Concepts, Rich, N, et al (ed.). pp. 87–97 (1983).

Zamora, P.O., et al., "A Second Tc–99m Binding Site In IgG Is Related To Distadine Groups," J. Nucl. Med., vol. 33, No. 5 (1992), Abstract No. 868.

Fischman, Alan J., et al., "A Ticket to Ride: Peptide Radiopharmaceuticals," *Journal of Nucl. Med.,* vol. 34, No. 12, pp. 2253–2263 (Dec. 1993).

IKVAV PEPTIDE RADIOPHARMACEUTICAL APPLICATIONS

CROSS-REFERENCE TO RELATED APPLICATIONS

This application is a continuation-in-part application of U.S. patent application Ser. No. 07/840,077, filed Feb. 20, 1992, now U.S. Pat. No. 5,443,816 entitled Peptide -Metal Ion Pharmaceutical Preparation and Method; and is related to U.S. Pat. No. 5,102,990, entitled Direct Radiolabeling of Antibodies and Other Proteins with Technetium or Rhenium; U.S. Pat. No. 5,078,985, entitled Radiolabeling Antibodies and Other Proteins with Technetium or Rhenium by Regulated Reduction; U.S. patent application Ser. No. 07/815,122, entitled Composition for Radiolabeling Antibodies and Other Proteins by Regulated Reduction; U.S. patent application Ser. No. 07/816,476, issued as U.S. Pat. No. 5,346,785 entitled Direct Radiolabeling of Antibody Against Stage Specific Embryonic Antigen for Diagnostic Imaging; U.S. patent application Ser. No. 07/816,477, issued as U.S. Pat. No. 5,460,785 on Oct. 24, 1995, entitled Direct Labeling of Antibodies and Other Proteins with Metal Ions; U.S. patent application Ser. No. 07/840,076, issued as U.S. Pat. No. 5,277,892 on Jan. 11, 1994, entitled Leukostimulatory Agent for In Vivo Leukocyte Tagging; U.S. patent application Ser. No. 07/864,470, issued as U.S. Pat. No. 5,277,893 on Jan. 11, 1994, entitled Direct Radiolabeling of Substrates Containing Monosulfides or Disulfide Bonds with Radionuclides; and a U.S. patent application filed on Dec. 30, 1992, as U.S. Ser. No. 07/998,910 entitled YIGSR Peptide Radiopharmaceutical Applications; the teachings of all of the foregoing which are incorporated herein by reference.

LICENSE RIGHTS

The U.S. Government has a paid-up license in this invention and the right in limited circumstances to require the patent owner to license others on reasonable terms as provided for by the terms of Small Business Innovative Research Grants No. 2 R44 CA50877 and 1 R43 CA58136 awarded by the National Institutes of Health, Department of Health and Human Services.

BACKGROUND OF THE INVENTION

1. Field of the Invention (Technical Field)

This invention relates to peptide-based metal ion-labeled compositions for use as pharmaceuticals, and particularly radiopharmaceuticals, for diagnostic imaging and therapeutic uses, and more particularly for differential diagnosis of various lung diseases, pathologies and abnormalities, and for localization, detection and treatment of cancerous tumors and other diseases and conditions.

2. Description of the Related Art, Including Information Disclosed under 37 C.F.R. Sections 1.97–1.99 (Background Art)

The use of biologically active peptides, which are peptides which bind to specific cell surface recentors, has received some consideration as radiopharmaceuticals. Canadian Patent Application 2,016,235, Labeled Chemotactic Peptides to Image Focal Sites of Infection or Inflammation, teaches a method of detecting a site of infection or inflammation, and a method for treating such infection or inflammation, by administration of a labeled or therapeutically-conjugated chemotactic peptide. In that application, the chemotactic peptides are chemically conjugated to DTPA and subsequently labeled with $^{111}$In. The utility of DTPA chelates covalently coupled to polypeptides and similar substances is well known in the art. Hnatowich, D J, U.S. Pat. Nos. 4,479,930 and 4,668,503. Other bifunctional chelates for radiolabeling peptides, polypeptides and proteins are well known in the art. Other biologically active peptides described include those disclosed by Olexa S A, Knight L C and Budzynski A Z, U.S. Pat. No. 4,427,646, Use of Radiolabeled Peptide Derived From Crosslinked Fibrin to Locate Thrombi In Vivo, in which iodination is discussed as a means of radiolabeling. In Morgan C A Jr and Anderson D C, U.S. Pat. No. 4,986,979, Imaging Tissue Sites of Inflammation, use of chelates and direct iodination is disclosed. In Tolman G L, U.S. Pat. No. 4,732,864, Trace-Labeled Conjugates of Metallothionein and Target-Seeking Biologically Active Molecules, the use of metallothionein or metallothionein fragments conjugated to a biologically active molecule, including peptides, is disclosed. The previous methods all employ some conjugation means with a bifunctional chelator in order to effectuate labeling with a radionuclide or other medically useful metal ion, such as a paramagnetic contrast agent. The only exception involves radioiodination; the iodine labeling of proteins or peptides containing tyrosine or histidine residues is well known, for example, by the chloramine-T, iodine monochloride, Iodogen or lactoperoxidase methods.

Pulmonary radionuclide imaging techniques currently in general practice involve the use of a) macroaggregated albumin or albumin microspheres (MAA), b) radioaerosols ($^{99m}$Tc-DTPA), c) radioactive gases, and d) gallium citrate. See, generally, Anger, K: Radionuclide Studies of the Lung, In: Sperber, M. (editor), *Radiologic Diagnosis of Chest Disease*, Springer-Verlag, New York, 1990, pp 140–153; Miller RF and O'Doherty M J: Pulmonary nuclear medicine. *Eur J Nucl Med* 19 (1992) 355–368. MAA is a radioactive particle which is sequestered by capillary blockade. After administration of radioactive particles greater than 10 µm in diameter into a peripheral vein, the pulmonary capillaries and precapillary arterioles act like a sieve, with the $^{99m}$Tc-MAA particles temporarily blocked so that the tracer is trapped in its first passage through the lung. The radioactivity distribution reveals relative pulmonary perfusion. When blood flow has been interrupted or significantly changed in a portion of the lung larger than 2 cm, a defect appears as a photon-deficient image. Most of the MAA particles (90%) have a diameter ranging from 10–40 µm. MAA particles degrade into smaller particles leaving the lung vasculature with a biologic half-time of 2–9 hours, and are cleared by phagocytosis in the reticuloendothelial system.

Many pulmonary diseases produce an altered pulmonary blood flow in the affected areas. Radiolabeled MAA allows detection of areas of altered blood flow, but provides no information related to any specific biochemical or metabolic event. Perfusion lung scintigraphy is highly sensitive, but not specific. Moreover, perfusion defects (13%) have been found in non-smoking volunteers without pulmonary disease, and loss of normal apex-to-base gradients (9%) have also been observed (Webber M M, Renick L H, Fouad B I, and Victery W K: Variants of the normal lung scan: Correlation with pulmonary function tests. *J Nucl Med* 13(1972) 476; Tetalman M R, Hoffer P B, Heck L L, et al: Perfusion scans in normal volunteers. *Radiology* 106(1973) 593–594). The lack of specificity can lead to mis-diagnosis, the need for additional test procedures, and delays in implementing therapy. Thus, there is a need for a diagnostic radiopharmaceutical which can overcome some or all of these problems.

The lung is an organ which can undergo extensive degradation and remodeling of the extracellular matrix as a result of disease. Emphysema, fibrosis, cancer and other chronic obstructive lung diseases all can lead to both microscopic and macroscopic alterations in air space, and related changes in the lung extracellular matrix and basement membrane. A radiopharmaceutical which can detect specific alterations in extracellular molecules or their receptors can be used as a specific probe of the biochemical and metabolic status of the lung in disease processes.

Laminin is a basement membrane glycoprotein ($M_r$=900,000) which has various biological activities including promoting cell attachment, growth, and differentiation. A typical laminin molecule consists of three polypeptide chains—A (440 kd), B1 (200 kd), and B2 (220 kd)—that are linked by disulfide bonds to form an asymmetric cross-structure. Multiple, distinct adhesive sequences in laminin appear to mediate specific biological functions, and bind to distinct cell surface receptors (Hynes R O: Integrins: versatility, modulation, and signaling in cell adhesion, *Cell* 69(1992) 11–25; Yamada K M: Adhesive recognition sequences, *J Biol Chem* 266(1992) 2809–2812).

One adhesive sequence from the laminin A-chain is Ile-Lys-Val-Ala-Val (IKVAV), (SEQ. ID NO. 1) and this peptide as well as longer laminin peptide sequences containing IKVAV (SEQ. ID NO. 1) have been reported to increase in vitro adhesiveness of a number of cell lines including mast cells (Thompson H L, Burbelo P D, Yamada Y, Kleinman H K, and Metcalfe D D: Identification of an amino acid sequence in the laminin A chain mediating mast cell attachment and spreading, *Immunology* 72(1991) 144–149; Thompson H L, Burbelo P D, Yamada Y, Kleinman H K, and Metcalfe D D: Mast cells chemotax to laminin with enhancement after IGE-mediate activation, *J Immunol* 143(1989) 4188–4192), cerebral cells (Tashiro K-I, Sephel G C, Weeks B, Sasaki M, Martin G R, Kleinman H K, and Yamada Y: A synthetic peptide containing the IKVAV sequence from the A chain of laminin mediates cell attachment, migration, and neurite outgrowth, *J Biol Chem* 27(1989) 16174–16182; Kleinman H K, Weeks B S, Cannon F B, Sweeney T M, Sephel G C, Clement B, Zain M, Olson M O J, Jucker M, Burrous B A: identification of a 100-kDa nonintegrin cell surface laminin-binding protein which recognizes an A chain neurite-promoting peptide. *Arch Biochem Biophys* 290(1991) 320–325; Skubitz A P N, Letourneau P C, Waynet E, and Furcht L T: Synthetic peptides from the carboxyl-terminal Globular domain of the A chain of laminin: their ability to promote cell adhesion and neurite outgrowth, and interact with heparin and the B1 integrin subunit. *J Cell Biol* 115(1991) 1137–1148; Sephel G C, Tashiro K-I, Sasaki M, Greatorex D, Martin G R, Yamada Y, and Kleinman H K: Laminin A chain synthetic peptide which supports neurite outgrowth, *Biochem Biophys Res Comm* 162 (1989) 821–829), normal mesenchymal cells (Kleinman et al., supra, 1991), tumor cells (Kleinman et al., supra, 1991), and hepatocytes (Clement B, SeGui-Real B, Savagner P, Kleinman H K, and Yamada Y: Hepatocyte attachment to laminin is mediated through multiple receptors, *J Cell Biol* 110(1990) 185–192). One such longer peptide, Cys-Ser-ArG-Ala-ArG-Lys-Gln-Ala-Ala-Ser-Ile-Lys-Val-Ala-Val-Ser-Ala-Asp-ArG (also referred to as PA22-2 ) (SEQ. ID NO. 2), increased in vivo lung colonization by melanoma cells (Kanemoto T, Reich R, Royce L, Greatorex D, Adler S H, Shiraishi N, Martin G R, Yamada Y, and Kleinman H K: identification of an amino acid sequence from the laminin A chain that stimulates metastasis and collagenase IV production, *Proc Nat Acad Sci* (USA) 87(1990) 2279–2283). The conformational status, but not specific chirality, of the IKVAV domain is a contributing factor in biological activity (Nomizu M, Utani A, Shiraishi N, Kibbey M C, Yamada Y, and Roller P R: The all-D-configuration segment containing the IKVAV sequence of laminin A chain has similar activities to the all-L-peptide in vitro and in vivo, *J Biol Chem* 267(1992) 14118–14121).

SUMMARY OF THE INVENTION (DISCLOSURE OF THE INVENTION)

In accordance with the present invention, a method of performing an administrative procedure in a patient, which procedure may be either diagnostic or therapeutic, is provided. In this method a medically useful metal ion-labeled peptide comprising a peptide sequence comprising the sequence IKVAV and a medically useful metal ion prepared and an effective amount administered to the patient. In one embodiment, the peptide is a peptide comprising the sequence SCRARKQAASIKVAVSADR (SEQ. ID NO. 2).

The method is most commonly employed for diagnostic procedures, with the preferred diagnostic procedure comprising imaging by metal ion detection means. Representative metal ion detection means include gamma scintigraphy, specific photon emission computerized tomography, positron emission tomography and magnetic resonance imaging. A variety of metal ions may be employed, including ionic elements of iron, cobalt, nickel, copper, zinc, arsenic, selenium, molybdenum, technetium, ruthenium, palladium, silver, cadmium, indium, antimony, rhenium, osmium, iridium, platinum, gold, mercury, thallium, lead, bismuth, polonium and astatine. These ionic elements will most generally be radioactive, paramagnetic and superparamagnetic.

The diagnostic procedure will most commonly involve diagnosis and detection of pathologies and disease of the lung. These pathologies and diseases can include chronic obstructive pulmonary diseases, such as emphysema and fibrosis, as well as primary lung carcinomas and metastatic cancers present in the lung.

In employing the method, the medically useful metal ion-labeled peptide can further comprise a chelating agent, whereby the medically useful metal ion is bound to the peptide via the chelating agent. The chelating agent can be a bifunctional agent.

Administration of the medically useful metal ion-labeled peptide is most commonly parenteral. It will generally be by intravenous injection, but may also be intradermal, subcutaneous, intramuscular, or intraperitoneal.

The medically useful metal ion-labeled peptide further can further include a metal ion-binding domain, such that the medically useful metal ion-labeled peptide comprises the sequence IKVAV and a metal ion-binding domain, whereby the linked medically useful metal ion is bound to the peptide via the metal ion-binding domain. In this situation, the peptide combination comprising the sequence IKVAV and a metal ion-binding domain can be selected from the group consisting of $(R_1)-[Y_1]_n-(R_2)$, $(R_1)-[Y_1-(R_2)-Y_1]_n-(R_3)$, and $(R_1)-[Y_1-(R_2)-Y_2]_n-(R_3)$ wherein the metal ion-binding domain comprises a member selected from the group consisting of $[Y_1]_n$, $[Y_1-(R_2)-Y_1]_n$ and $[Y_1-(R_2)-Y_2]_n$ wherein n is a number between 1 and about 6, and $Y_1$ and $Y_2$ are amino acids comprising at least one element selected from the group consisting of sulfur, nitrogen or oxygen which is available or can be made available for binding to metal ions;

the peptide sequence IKVAV comprises at least one member selected from the group consisting (SEQ. ID NO. 1) of $R_1$, $R_2$ and $R_3$ and further comprises an amino acid sequence containing from 5 to about 20 amino acids; and those portions of $R_1$, $R_2$ and $R_3$ not comprising the peptide sequence IKVAV (SEQ. ID NO. 1) each comprise an amino acid sequence containing from 0 to about 20 amino acids.

In those methods employing a metal ion-binding domain, that domain may comprise at least one amino acid sequence selected from the group Consisting of cysteine, cystine, histidine, penicillamine, deacylated methionine, lysine, arginine, aspartic acid, glutamic acid and tyrosine. Most commonly, the metal ion binding domain will be selected from the group $[Cys]_n$,
$[Cys-(R_2)-Cys]_n$,
$[Cys-(R_2)-Pen]_n$,
$[His-(R_2)-Cys]_n$,
$[His-(R_2)-Pen]_n$,
$[His]_n$, and
$([His-(R_2)-His]_n$ wherein n is a number between 1 and about 6; and $R_2$ is an amino acid sequence containing from 1 to about 20 amino acids.

The present invention also provides a peptide-based pharmaceutical composition, which may be lyophilized, suitable for administration to a patient for diagnostic imaging of the lung, comprising a peptide which substantially targets the lung, and further comprising, in part, a medically useful metal ion-binding domain. The peptide-based pharmaceutical composition may further comprise a metal ion labeling agent, and may also further comprise a medically useful metal ion. The peptide-based pharmaceutical composition may also further comprise a biological-function domain which comprises the peptide sequence IKVAV (SEQ. ID NO. 1). This composition which includes a biological-function domain which comprises the peptide sequence IKVAV (SEQ. ID NO. 1) and a medically useful metal ion-binding domain is selected from the group consisting of $(R_1)-[Y_1]_n-(R_2)$,
$(R_1)-[Y_1-(R_2)-Y_1]_n-(R_3)$, and
$(R_1)-[Y_1-(R_2)-Y_2]_n-(R_3)$ wherein the medically useful metal ion-binding domain comprises a member selected from the group consisting of $[Y_1]_n$, $[Y_1-(R_2)-Y_1]_n$ and $[Y_1-(R_2)-Y_2]_n$ in which n is a number between 1 and about 6 and $Y_1$ and $Y_2$ are amino acids comprising at least one element selected from the group consisting of sulfur, nitrogen or oxygen which is available or can be made available for binding to metal ions;

the biological function domain comprising the peptide sequence IKVAV (SEQ. ID NO. 1) further comprises at least one member selected from the group consisting of $R_1$, $R_2$ and $R_3$; and those portions of $R_1$, $R_2$ and $R_3$ not comprising the biological-function domain comprising the peptide sequence IKVAV (SEQ. ID NO. 1) each comprise an amino acid sequence containing from 0 to about 20 amino acids.

One peptide-based pharmaceutical composition which may be employed wherein the peptide comprising a biological-function domain which comprises the peptide sequence IKVAV (SEQ. ID NO. 1) and a medically useful metal ion-binding domain is a peptide comprising the sequence SCRARKQAASIKVAVSADR (SEQ. ID NO. 2).

The medically useful metal ion-binding domain of the peptide-based pharmaceutical composition may include amino acid sequences containing cysteine, cystine, histidine, penicillamine, deacylated methionine, lysine, arginine, aspartic acid, glutamic acid and tyrosine. Specific medically useful metal ion-binding domains include the following:

$[Cys]_n$,
$[Cys-(R_2)-Cys]_n$,
$[Cys-(R_2)-Pen]_n$,
$[His-(R_2)-Cys]_n$,
$[His-(R_2)-Pen]_n$,
$[His]_n$, and
$([His-(R_2)-His]_n$ wherein n is a number between 1 and about 6; and $R_2$ is an amino acid sequence containing from 1 to about 20 amino acids.

The metal ion labeling agent in the peptide-based pharmaceutical composition can be a stannous ion agent, which may be present in a solution comprising alkali metal tartrate. The solution may also comprise dicarboxylic acids, such as phthalate, tartrate and citrate. The stannous ion agent can include stannous tartrate, stannous glucoheptonate, stannous gluconate, stannous phosphonate, stannous chloride, or stannous fluoride.

Accordingly, it is an object of the present invention to provide for pharmaceutically useful peptides comprising a biological-function domain containing the sequence IKVAV (SEQ. ID NO. 1) and a linked metal ion.

It is a further object of the present invention to provide a means whereby diseases, pathologies and abnormalities of the lung can be diagnosed and treated.

It is a further object of the present invention to provide a means whereby metal ion-binding domains can be directly synthesized or genetically introduced into a peptide comprising a biological-function domain containing the sequence IKVAV (SEQ. ID NO. 1), thereby allowing labeling without the necessity of conjugation to bifunctional chelators.

Another object of the present invention to provide a method for performing a diagnostic procedure by administration of a metal ion-labeled peptide composed of a biological-function domain containing the sequence IKVAV (SEQ. ID NO. 1) and a metal ion-binding domain.

Another object of the present invention is to provide a method for the direct labeling of peptides comprising a biological-function domain including the sequence IKVAV (SEQ. ID NO. 1), and which peptides further comprise amino acid sequences containing amino acids with sulfur, nitrogen or oxygen which is available or can be made available for binding metal ions, such as cysteine, histidine or penicillamine, or some combination thereof.

It is a further object of the present invention to provide a method to label peptides containing a biological-function domain including the sequence IKVAV (SEQ. ID NO. 1) with medically useful metal ions without loss of the biological function of the peptide due to the labeling process.

Another object of the present invention is to provide a method and product which permits labeling to be accomplished by the end user using a single vial, containing a peptide with a biological-function domain comprising at least the sequence IKVAV (SEQ. ID NO. 1) and a medically useful metal ion binding domain and a metal ion labeling agent, which method requires only a single step to accomplish labeling, being the introduction of the medically useful metal ion.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION

(BEST MODES FOR CARRYING OUT THE INVENTION)

Using the methods of this invention, peptides with a biological-function domain comprising at least the sequence IKVAV and a linked radiolabel provide materials useful for in vivo diagnostic applications, particularly for diagnostic imaging of the lungs. Preferably, the peptide comprises a biological-function domain of at least the sequence IKVAV (SEQ. ID NO. 1) and a metal-ion binding domain comprising metal ion binding sequences which can be coupled directly with metal ions. The peptides can be prepared in a format providing a labeling kit which can, in turn, be used to prepare a metal ion-peptide complex for in vivo use. It is also possible to provide for labeling of a peptide with the biological-function domain with a metal ion in vivo, such as through use of a peptide-avidin complex, which is injected in vivo, followed by a biotin-metal ion complex inject in vivo, resulting in formation of an in vivo peptide-avidin-biotin-metal ion complex. The peptides of this invention preferably contain:

a) biological-function domains comprising at least the sequence IKVAV, and b) metal ion-binding domains which can complex with medically useful metal ions.

The terms "bind," "binding," "complex," and "complexing," as used throughout the specification and claims, are intended to cover all types of physical and chemical binding, reactions, complexing, attraction, chelating and the like.

The biological-function domain of the preferred peptide is defined in the specification and claims as a sequence of the amino acids Ile-Lys-Val-Ala-Val (IKVAV single amino acid code (SEQ. ID NO. 1)), and optionally amino acids in addition to IKVAV (SEQ. ID NO. 1) which are useful for lung imaging and treatment. The IKVAV (SEQ. ID NO. 1) peptide of this invention will, for the most part, include the sequence RKQAASIKVAV (SEQ. ID NO. 3), and most preferably the sequence CSRARKQAASIKVAVSADR (SEQ. ID NO. 2). Usually, within the indicated sequences, there may be mutations, including deletions, insertions or substitutions. It is possible that the sequence IKVAV (SEQ. ID NO. 1) may be repeated one or more times, to increase localization. For the most part, substitutions will be conservative, in which amino acids having substantially the same conformation and polarity may be employed. The peptides may use L-amino acids, or one or more of the amino acids may be substituted by D-amino acids (D-stereoisomer), which may in part increase resistance to protease degradation. Particularly, one or more alanines may be substituted. In the alternative, terminal amino acids may be employed having unnatural chirality. The peptide may also include a terminal amide or a terminal acylated amino acid, particularly acetylated or alkylated, particularly methylated, amino acids. Where a cysteine provides the metal-ion binding domain at the N-terminus, the cysteine may be alkylated or unsubstituted on the mercaptan group.

It is hypothesized, without wishing to bind the inventor herein, that lung localization is receptor-based, and due in part to pulmonary endothelial cell binding, and in some instances to tumor receptor binding. There is also evidence to suggest that IKVAV-containing peptide binds to receptors on tissue plasminogen activator, which is frequently present in relative high concentrations in tumor cells. Regardless of the exact mechanism of receptor-based lung localization, such a mechanism presents significant advantages for a $^{99m}$Tc-peptide containing the IKVAV sequence over $^{99m}$Tc-MAA:

a) The peptide should not itself alter pulmonary perfusion, b) The peptide should bind to pre-capillary, capillary, and post-capillary endothelial cells and thereby, provide a more representative view of the actual physiology of the lung vasculature, c) The use of a synthetic peptide for imaging would obviate considerations relating to viral (HIV or the like) contamination of the source material, d) The use of a non-particulate imaging agent should minimize health risks in hyper-sensitive patient populations, such as pediatric use;

e) Differential diagnosis of certain conditions may be possible, in that chronic obstructive conditions such as emphysema will be detected as photon-deficient, and certain tumors will be detected as photon-rich.

The metal ion-binding domain of the peptide is defined in the specification and claims as a sequence of one or more amino acids containing sulfur, nitrogen or oxygen which is available for binding or can be made available for binding to metal ions. Sulfur-containing amino acids include primarily cysteine (Cys), cystine (Cys-Cys) and penicillamine (Pen), although deacylated methionine (Met) and other amino acids may also be used. Useful nitrogen-containing amino acids include primarily histidine (His), but under certain conditions lysine (Lys) and arginine (Arg), which have $pK_a$ values of 10.0 and 12.0, and other amino acids, may also be employed. In addition, the terminal amino group of peptides may also be employed. Useful oxygen-containing amino acids include aspartic acid (Asp), glutamic acid (Glu) and tyrosine (Tyr), as well as the terminal carboxyl group of peptides and other amino acids. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domain may employ L-amino acids, or one or more of the amino acids may be substituted by D-amino acids (D-stereoisomer). The metal ion-binding domains may occur once or multiple times in any given peptide, and may occur in any combination. The metal ion-binding domain and the biological-function domain may overlap.

The metal binding sequences as found in the peptides of this invention may be stabilized by the addition of a positively-charged transition metal ion of Zn, Cu, Sn, Co, or Ni, or the like, selected to have a low order of binding strength. Through a replacement reaction, the transition metal ion replaces the H ion of the thiolate, imidazole or carboxyl group. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer. The buffer may comprise dicarboxylic acids (tartrate, phthalate, citrate), amino acids (glycine, di-glycine, tri-glycine), borate or the like. For radiolabeling in acidic conditions typically 10 mM tartrate and 40 mM phthalate, pH about 5 to about 7, are used. For radiolabeling in basic conditions typically 10 mM glycine, pH about 8 to about 10, is used. The buffer may also contain a number of excipients and/or stabilizers including NaCl, inositol, glucoheptonate, or the like.

The peptide of this invention is reacted with a medically useful metal ion. The medically useful metal ion may be radioactive and generate gamma rays, beta particles, or positrons which are converted into gamma rays upon collision with electrons. Alternatively, the medically useful metal ion may be paramagnetic or superparamagnetic. The medically useful metal ion may used in diagnostic imaging procedures including gamma scintigraphy, specific photon emission computerized tomography, positron emission tomography or magnetic resonance imaging.

Particularly useful metal ions can be found in the group consisting of elements 26–30 (Fe, Co, Ni, Cu, Zn), 33–34 (As, Se), 42–50 (Mo, Tc, Ru, Rh, Pd, Ag, Cd, In, Sn) and 75–85 (Re, Os, Ir, Pt, Au, Hg, Tl, Pb, Bi, Po, At). Isotopes of the elements Tc, Re, and Cu are particularly applicable for use in diagnostic imaging and radiotherapy. The isotope $^{99m}$Tc is particularly applicable for use in diagnostic imaging. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi. The type of medically useful metal ion depends on the specific medical application. The medically-useful metal ion is selected to have a higher order of binding than the positively charged-transition metal ion used to stabilize the metal binding sequences. Radioisotopes of Tc are of significant interest, and particularly $^{99m}$Tc. In the case of $^{99m}$Tc, the peptides are reacted with sodium pertechnetate which has been treated with a reducing agent to generate Tc with a lower oxidation state. The product of the reaction between the metal ion and the peptide is a complex of the metal ion and the peptide. For example, the following structures could result from use of the invention, using Tc labeling of peptides containing metal-ion binding domains consisting of Cys and His groups as an example:

a) 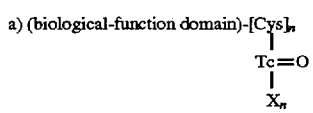

b) 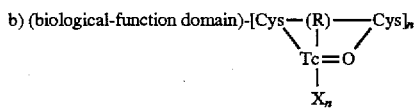

c) 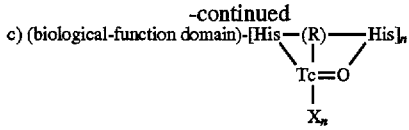

wherein R is an amino acid sequence containing from 0 to about 20 amino acids and $X_n$ is an anion, such as a halogen (e.g. fluoride or chloride), or a solvent molecule, such as water. In the foregoing, the biological-function domain is a peptide sequence including at least the amino acids IKVAV.

The resulting Tc-peptide bond should have a sufficiently high bond strength to minimize the exchange of the radionuclide to transferrin and serum albumin. The complex should be thermodynamically stable under varying physiological conditions and exhibit acceptable toxicological properties.

Most stannous reductions are performed at a pH of from about 5 to about 6. With amino acid side chains in a solution at pH 5.6, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 6 only Cys and His are optimal $^{99m}$Tc binding site candidates. For both Cys and His, radiolabeling yields are dependant on pH, and are theoretically optimal at or near the $pK_a$.

It is also possible to administer the IKVAV-containing peptide, and to perform the actual radiolabeling in vivo. This can be done, for example, using a biotin-avidin system, in which biotin is conjugated to the IKVAV-containing peptide, which is then injected into the patient. A radioisotope-labeled avidin complex is then injected, which binds to the peptide-biotin complex, forming a peptide-biotin-avidin-radiolabel complex, which can be detected by gamma scintigraphy or other detection means. This method presents certain advantages, in that maximum clearance and target binding parameters can be attained. To use this system, for example, it is possible to employ Biotin-HPDP (Pierce Chemical Co.), a clearable, sulfhydryl-reactive biotinylation reagent. The IKVAV-containing peptide is dissolved in a 100 mM borate buffer pH 8.0 to a final concentration of 1 mg/ml, and biotin-HPDP at 1 mg/ml is added. The solution is mixed and incubated for 1 hour, and the biotinylated peptide separated from unconjugated materials by molecular sieve chromatography over Sephadex G-25. Avidin or strepavidin can be directly iodinated with $^{131}$I by standard methods. Alternatively, avidins can be conjugated to chelating agents such as DTPA or other agents which introduce thiols into the protein, and radiolabeled with $^{99m}$Tc. For use in vivo, the biotinylated peptide is injected intravenously and allowed to localize and clear from the general circulation, a time period generally of from 1 to 2 hours. Radiolabeled avidin is then injected; the radiolabeled avidin binds to the biotin, and consequently localizes the disease lesion.

The peptides of the invention can be:
  a) naturally-occurring,
  b) produced by chemical synthesis,
  c) produced by recombinant DNA technology,
  d) produced by biochemical or enzymatic fragmentation of larger molecules,
  e) produced by methods resulting from a combination of a–d, or
  f) produced by any other means for producing peptides.
By employing synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like. The peptides can also include peptide fragments, polypeptides and other like structures, generally consisting of a sequence of amino acids. The peptides can also include fragments of laminin, a basement membrane glycoprotein, including specifically fragments of the polypeptide chain of laminin containing the adhesive sequence IKVAV (SEQ. ID NO. 1). The laminin may itself be natural or produced by any means. For the most part, the peptides of this invention comprise fewer than 60 amino acids, preferably fewer than 30 amino acids, and most preferably ranging from about 10 to 30 amino acids. The term "peptide" as used throughout the specification and claims is intended to include all of the foregoing.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

The product may be used to monitor or treat normal or abnormal tissues and metabolic events, particular chronic obstructive pulmonary disease, such as emphysema or fibrosis, in which abnormal tissues or metabolic events will generally produce a photon-deficient area, and to localize primary or metastatic cancerous tumors, and particularly cancerous tumors of the lung, in which cancerous tumors will generally produce a photon-abundant area.

In Rhodes B A and Zamora P O, U.S. Pat. No. 5,460,785, entitled Direct Labeling of Antibodies and Other Proteins with Metal Ions, a method is taught in which a protein substrate, including peptides, containing monosulfides or disulfide bonds is labeled with a medically useful metal ion by the following method:

a) incubating the protein with a reducing agent to reduce some or all of the disulfide bonds to thiolate groups, or to maintain monosulfides as thiolate groups;

b) removing excess reducing agent from the protein substrate containing thiolate groups;

c) adding a source of Sn (II) agent to the thiolate-containing protein preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing protein form metal ion-containing and sulfur-containing complexes.

This invention also teaches that it is possible to chemically modify the protein by the introduction of disulfide bonds. A protein, even though it may not natively contain monosulfides or disulfide bonds, with attached or complexed disulfide bonds can be labeled. The discussions therein pertaining to medically useful metal ions are also appropriate for use with peptides described herein which contain cysteine or penicilleumine, and thus contain one or more disulfide bonds or one or more monosulfides. Accordingly, the teachings of this application are incorporated herein by reference.

In Rhodes B A, U.S. Pat. No. 5,277,892, entitled Leukostimulatory Agent for In Vivo Leukocyte Tagging, the use of a variety of leukostimulatory substances, including lectins, peptides and immunoglobulins, labeled or to be labeled with medically useful metal ions, is taught. These teachings, which also involve labeling through disulfide bonds or monosulfides, are specifically applicable to peptides containing cysteine or penicillamine. According, the teachings of that application are incorporated herein by reference.

In Zamora P O and Rhodes B A, U.S. Pat. No. 5,443,816, entitled Peptide-Metal Ion Pharmaceutical Preparation and Method, the use of peptide-based metal-ion labeled compositions as pharmaceuticals is .taught, together with methods of labeling peptides, proteins and other similar substances with radiometals, paramagnetic metals and other medically useful metal ions. This invention also teaches that peptides containing a biological-function domain and a medically useful metal ion-binding domain can be labeled with medically useful metal ions for use in diagnosis and treatment of a variety of pathologic conditions. Specific medically useful metal-ion labeled peptides for detection of thrombus, cancer, infection and inflammation are provided. Accordingly, the teachings of this application are incorporated herein by reference.

In Zamora P O, United States patent application filed on Dec. 20, 1992, as U.S. Ser. No. 07/998,910, entitled YIGSR Peptide Radiopharmaceutical Applications, the use of peptides containing a biological-function domain which includes the sequence Tyr-Ile-Gly-Ser-Arg (YIGSR) (SEQ. ID NO. 4) and medically useful metal ion-binding domain are labeled with medically useful metal ions for use in a variety of diseases and pathologic conditions, and particularly for diagnosis and treatment of thrombosis and other diseases and conditions. Accordingly, the teachings of this application are incorporated herein by reference.

The metal ion-binding domain of the peptide involves one or more amino acids containing sulfur, nitrogen or oxygen which is available for binding, or which can be made available for binding to metal ions. Commonly used amino acids include Cys, Pen and His, or any combination of them. The simplest case takes the form

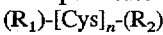

$(R_1)\text{-}[Cys]_n\text{-}(R_2)$ wherein $[Cys]_n$ is the medically useful metal ion-binding domain and n is typically a number between 1 and about 6; and $R_1$ and $R_2$ are each an amino acid sequence containing from 0 to about 20 amino acids, with at least $R_1$ and $R_2$ including the biological-function domain. In this and all related forms, it should be noted that $R_1$ and $R_2$ are interchangeable; either can contain the biological-function domain, the biological-function domain may include part or all of both $R_1$ and $R_2$, and the biological-function domain may constitute only a portion of the amino acid sequence in either $R_1$ or $R_2$. The order of components for these purposes can be varied, so that $(R_1)\text{-}[Cys]_n\text{-}(R_2)$, $(R_2)\text{-}[Cys]_n\text{-}(R_1)$, $[Cys]_n\text{-}(R_2)\text{-}(R_1)$, $[Cys]_n\text{-}(R_1)\text{-}(R_2)$ and the mirror images of the last two orderings are all equivalent, even though the resulting peptides may significantly differ in other aspects. A representative example of this form is the sequence Cys-Ser-ArG-Ala-ArG-Lys-Gln-Ala-Ala-Ser-Ile-Lys-Val-Ala-Val-Ser-Ala-Asp-Arg (SEQ. ID No. 2)

in which the Cys is $[Cys]_n$ wherein n is 1, Ile-Lys-Val-Ala-Val (IKVAV) is the biological-function domain and is included in $R_1$ and the remainder of the sequence is $(R_2)$, so that the structure of the sequence is $[Cys]_n\text{-}(R_1)\text{-}(R_2)$.

Other forms of the same general configuration include $(R_1)\text{-}[Cys\text{-}(R_2)\text{-}Cys]_n\text{-}(R_3)$, $(R_1)\text{-}[Cys\text{-}(R_2)\text{-}Pen]_n\text{-}(R_3)$ , $(R_1)\text{-}[His\text{-}(R_2)\text{-}Cys]_n\text{-}(R_3)$, $(R_1)\text{-}[His\text{-}(R_2)\text{-}Pen]_n\text{-}(R_3)$ , and $(R_1)\text{-}[His\text{-}(R_2)\text{-}His]_n\text{-}(R3)$ wherein the sequence $[...]_n$ is the medically useful metal ion-binding domain with n typically being a number between 1 and about 6; and $R_1$, $R_2$ and $R_3$ are each an amino acid sequence containing from 0 to about 20 amino acids with at least one of $R_1$, $R_2$ and $R_3$ including the biological-function domain which includes at least the sequence IKVAV (SEQ. ID NO. 1). Here too the ordering is irrelevant to the functional description; for example, $(R_3)$-[His-$(R_2)$-Cys]$_n$-$(R_1)$, $(R_1)$-$(R_3)$-[His-$(R_2)$-Cys]$_n$, $(R_3)$-$(R_1)$-[His-$(R_2)$-Cys]$_n$, mirror images of the foregoing two orderings, all orderings in which the positions of His and Cys are reversed, and orderings in which the biological-function domain is present in any of the three regions $R_1$, $R_2$ and $R_3$, any portion of the three regions $R_1$, $R_2$ and $R_3$, or any combination of the three regions $R_1$, $R_2$ and $R_3$, are all equivalent to the third configuration listed above, $(R_1)$-[His-$(R_2)$-Cys]$_n$-$(R_3)$. Each of the other foregoing configurations can be similarly described.

In one preferred embodiment of the method for labeling peptides of the configurations set forth above, the following method can be employed:

a) adding a source of positively-charged transition metal, most preferably a Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof; and, b) adding a medically useful metal ion whereby the metal ion displaces the transition metal in the transition metal-containing and sulfur-, nitrogen- or oxygen-containing complexes and the metal ion and peptide form metal ion-containing and sulfur-, nitrogen-, or oxygen-containing complexes.

The preferred transition metal is Sn (II); useful sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is prepared in a buffer composed of 10 mM tartrate and 40 mM phthalate, pH 5.6, and is added to peptide to yield a final concentration of 1 mg/ml peptide solution.

Sn (II) can be stabilized by use of dicarboxylic acids, such as phthalate and tartrate. A wide range of dicarboxylic acids, known to those skilled in the art, may be similarly used to stabilize the Sn (II) and/or to act as a buffer. If the phthalate and tartrate are in molar excess relative to the Sn (II), then these dicarboxylic acids also stabilize the medically useful metal ion in a form which can react with the peptide. In one embodiment tartrate and phthalate are used in the Sn (II) agent at concentrations of 10 mM and 40 mM, respectively.

Similarly, the Sn (II) and the medically useful metal ion may be stabilized by free amino acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0.1–10 mM.

The peptide may be stored in bulk form or in unit dose form after addition of the Sn (II) or other transition metal. For example, in one embodiment the peptide is stored at $-20°$ C. in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 µg of Sn (II), 500 µg of peptide, 2 mg/ml of glycine, and 2 mg/ml of inositol. To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radiolabeled preparation can be directly used in medical applications.

In the embodiment in which $^{99m}$Tc is used, the Sn (II) is present in the peptide-containing solution in sufficient excess to alter the oxidation state of the Tc ion such that it can bind to ionizable groups. Similar approaches may be used to lower the oxidation state of other medically useful metal ions for subsequent binding to ionizable groups. The type of the metal ion, its isotopic nature, and concentration would depend on the intended medical application.

It is also possible to construct a peptide wherein the biological-function domain contains the sequence IKVAV and the peptide further contains a metal ion-binding domain including one or more disulfide bonds. In that case, it is necessary to first reduce the disulfide bond or bonds. In a preferred method, the following steps are employed:

a) incubating the peptide with a reducing agent to reduce some or all of the disulfide bonds to thiolate groups;

b) removing excess reducing agent from the peptide substrate containing thiolate groups;

c) adding a source of Sn (II) agent to the thiolate-containing peptide preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the claims are not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

Different configurations of peptide with one or more disulfide bonds are possible, and can be labeled as set forth herein. The most common example is the form

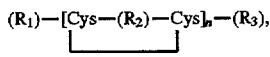

wherein [Cys-($R_2$)-Cys]$_n$ is the medically useful metal ion-binding domain, which can appear in the amino acid sequence from 1 time to about 6 times; and $R_1$, $R_2$ and $R_3$ are each amino acid sequences containing from 0 to about 20 amino acids, with at least one of the amino acid sequences $R_1$, $R_2$ and $R_3$ comprising the biological-function domain IKVAV (SEQ. ID NO. 1). Other peptide configurations in which reducible disulfide bonds are present are also included in this method. These include the substitution of Pen for one or both Cys amino acids, as well as the modification of a native Met to allow it to form a disulfide bond. The biological-function domain can appear in any one of $R_1$, $R_2$ and $R_3$, and can also span more than one region, so that the biological-function domain may comprise, for example, $R_2$ and $R_3$, or some portion of $R_2$ and $R_3$. Any one or more of the regions $R_1$, $R_2$ and $R_3$ may contain no amino acids.

Numerous reducing agents have been described and are known to those skilled in the art. Particularly useful types of reducing agents include 2-mercaptoethanol; 1,4-dithiotheitol; 2,3-dihydroxybutane-1,4-dithiol; 2-aminoethanethiol HCl; 2-mercaptoethylamine; thioglycolate; cyanide; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are normally employed than is required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/ml. The reduction reaction is allowed to proceed for a period of time at room temperature, three hours having been employed successfully with some peptides containing a single disulfide bond, after which time the reaction is terminated by removing excess Sn (II) ions by molecular sieve chromatography. One means of molecular sieve chromatography employs Sephadex G-25, with the chromatography gel pre-equilibrated, and the peptide eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forms of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) is believed to minimize the reformation of disulfide bonds. Sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment, stannous tartrate is used at a concentration of 1.25 mM. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/ml peptide solution.

The invention is further illustrated by the following non-limiting examples.

EXAMPLE 1

PREPARATION OF PEPTIDE KITS FOR $^{99m}$Tc LABELING

Laminin-derived peptide of the sequence CSRARKQAASIKVAVSADR (SEQ. ID NO. 2) was obtained commercially (Bachem, inc.) as lyophilized powder and used without additional purification. The N-terminal thiolate associated with the Cys residue was used as the metal ion-binding domain for subsequent labeling with reduced $^{99m}$Tc.

Peptide labeling kits were prepared aseptically using nitrogen-purged solutions, and whenever feasible under an atmosphere of nitrogen. To prepare the peptide labeling kits, the peptide was dissolved to a final concentration of 1.4 mg/ml in chilled, nitrogen-purged 10 mM tartrate/40 mM phthalate buffer, pH 5.6 (P/T buffer) containing 2% maltose. The peptideo and P/T buffer solution was then mixed (7:3) with P/T buffer containing 1.25 mM stannous tartrate. Aliquots (typically 0.5 ml containing 500 µg of peptide) were then sterile filtered through a 0.22 micron filter, and dispensed into individual vials. The head space of each vial was purged with nitrogen, the vials stoppered and crimped, and stored frozen at −70° C.

EXAMPLE 2

$^{99m}$Tc LABELING OF PEPTIDE KITS

To radiolabel, a vial of the preparation of Example 1 was removed from the freezer and allowed to come to room temperature. The labeling reaction was initiated by the addition of 0.5–2.0 mCi of $^{99m}$Tc (sodium pertechnetate in saline). Radiochemical analysis was begun 30 minutes after the introduction of the pertechnetate.

EXAMPLE 3

RADIOCHEMICAL ANALYSIS BY CHROMATOGRAPHY

To determine the relative amount of $^{99m}$Tc bound to a given peptide preparation, aliquots of the $^{99m}$Tc-labeled preparations were analyzed by molecular sieve HPLC, reverse phase chromatography, and thin layer chromatography.

Molecular sieve HPLC was performed using a 7.5×300 mm TSK G3000SW column preceded with a TSK-SW 7.5×7.5 mm guard column (TosoHaas, Philadelphia, Pa.) at a flow rate of 1 ml/minute of a phosphate buffered saline solution (0.01 M phosphate, pH 7.0, containing 0.15 M NaCl), with a UV and radioisotope detector in series. The preparation of Example 1 eluted at 12.8 minutes with a low chromatographic recovery (less than 10%). In control studies, pertechnetate eluted at 17.8 minutes with essentially quantitative chromatographic recovery.

For reverse-phase analysis, Sep-Pak $C_{18}$ mini-columns (Millipore Inc., Bedford, Mass.) were used as reverse-phase adsorbents to evaluate the binding of $^{99m}Tc$ to the peptides. The coles were rinsed with 10 ml of 100% ethanol followed by 10 ml of 0.001% HCl. Aliquots of 100 µl of the test sample were loaded onto the column and the unbound material eluted with 10 ml of 0.001% HCl. The column was then serially eluted with a graded series of 10 ml solutions of aqueous ethanol (10%, 20%, 30%, 40%, 50%, 60%, and 100%). The radioactivity in each eluant fraction (0.001% HCl through 100% ethanol) was determined by counting an aliquot (20 µl) of each fraction in a gamma scintillation counter. The columns themselves were also counted, after allowing an appropriate time for decay. All counts were corrected for decay and the amounts of radioactivity in each fraction expressed as a percentage of the total radioactivity assayed. The reverse-phase chromatography using $C_{18}$ mini-columns eluted with a graded series of ethanol confirmed $^{99m}Tc$ binding to the peptide (Table 1).

TLC was used to measure the amount of peptide-bound (and unbound) $^{99m}Tc$ and the amount of radiolabeled aggregate/colloid. Both measurements involved the use of ITLC-SG (Gelman Sciences, #61886) chromatography paper, cut into 1.5×10 cm strips and activated by heating for 30 minutes at 110° C., as per the manufacturer's instructions. After heating, the strips were stored at room temperature until use.

Peptide-bound $^{99m}Tc$ in the radiolabeled preparations was measured using TLC in 85% aqueous methanol using ITLC-SG strips. The solvent separated the soluble, unbound $^{99m}Tc$ (which migrates with the solvent front) from $^{99m}Tc$ bound to the peptide (which remains at the origin). Percentage of unbound $^{99m}Tc$ was expressed as CPM in the origin half of the strip divided by the total CPM, with all measures corrected for background.

Thin layer chromatography of the preparation of Example 1 in saline over heat-activated silica-gel coated cellulose (ITLC-SG paper) showed essentially all radioactivity associated with the peptide ($R_f=0$). The preparations did not contain significant amounts of unbound $^{99m}Tc$ as pertechnetate or $^{99m}Tc$-tartrate ($R_f=1.0$).

TABLE 1

Elution of $^{99m}Tc$-peptide preparation of Example 1 from $C_{18}$ reverse-phase columns by increasing concentrations of ethanol. Tartrate was used in the kits as a $^{99m}Tc$ transfer agent. In the absence of peptide tartrate retains $^{99m}Tc$, and its elution is provided here as a reference.

| Percent EtOH in Eluent | PERCENTAGE OF TOTAL RADIOACTIVITY ASSAYED | |
|---|---|---|
| | $^{99m}Tc$-Tartrate | $^{99m}Tc$-Peptide |
| 0% | 90.9% | 0.8% |
| 10% | 2.2% | 0.9% |

TABLE 1-continued

Elution of $^{99m}Tc$-peptide preparation of Example 1 from $C_{18}$ reverse-phase columns by increasing concentrations of ethanol. Tartrate was used in the kits as a $^{99m}Tc$ transfer agent. In the absence of peptide tartrate retains $^{99m}Tc$, and its elution is provided here as a reference.

| Percent EtOH in Eluent | PERCENTAGE OF TOTAL RADIOACTIVITY ASSAYED | |
|---|---|---|
| | $^{99m}Tc$-Tartrate | $^{99m}Tc$-Peptide |
| 20% | 1.6% | 0.2% |
| 30% | 0.8% | 0.3% |
| 40% | 0.5% | 0.5% |
| 50% | 0.8% | 0.3% |
| 60% | 0.5% | 0.3% |
| 100% | 1.1% | 0.4% |
| On Column | 1.6% | 95.7% |

EXAMPLE 4

BIODISTRIBUTION IN RODENTS

The biodistribution of the $^{99m}Tc$-peptide of Example 1 was evaluated in adult female Swiss-Webster mice (approximately 19 g) at selected times (10, 30, and 120 minutes) after injection into the tail vein. Each experimental group was composed of at least five animals, with each animal receiving 0.1 ml containing 5 µg of peptide (1 µCi/µg). Animals were sacrificed by Halothane overdose, and selected organs dissected, weighed, and associated radioactivity determined. Data were analyzed using a computer program specifically designed for $^{99m}Tc$-labeled preparations. The percent dose per organ for blood, bone, and muscle were calculated assuming 7, 8.2, and 40% of total body weight, respectively, for these tissues.

Following the injection of $^{99m}Tc$-peptide of Example 1, a significant amount of radioactivity was found in the lungs at both 10 and 30 minutes post injection (Table 2). Major accumulations were also found in the liver and kidneys. By two hours post injection the amount of radiolabel in the lung had fallen to less than 5% (from 47% at 10 minutes post injection, with a concomitant increase in kidney activity noted). Only small uptakes of $^{99m}Tc$ were noted in other organs. At 10 and 30 minutes post injection the lung-to-blood ratios for $^{99m}Tc$-peptide of Example 1 were 21:1 and 23:1, respectively.

TABLE 2

Biodistribution of $^{99m}Tc$-peptide of Example 1 in normal Swiss-Webster mice at selected times after injection. All values are the mean ± standard deviation. n = 6 for all data points.

| ORGAN | % INJECTED DOSE/ORGAN | | | | | |
|---|---|---|---|---|---|---|
| | 10 MINUTES | | 30 MINUTES | | 120 MINUTES | |
| blood | 10.5 | 1.0 | 7.6 | 1.0 | 6.9 | 1.7 |
| stomach | 0.5 | 0.1 | 0.7 | 0.2 | 0.6 | 0.1 |
| sm. intestine | 1.4 | 0.1 | 2.3 | 0.5 | 3.5 | 0.1 |
| appendix | 0.2 | 0.0 | 0.2 | 0.0 | 1.4 | 0.3 |
| lg. intestine | 0.3 | 0.1 | 0.2 | 0.1 | 0.9 | 0.3 |
| liver | 14.3 | 1.4 | 17.3 | 1.9 | 27.5 | 5.7 |
| spleen | 2.2 | 0.5 | 3.1 | 0.3 | 2.1 | 5.7 |
| kidneys | 7.4 | 0.6 | 12.2 | 1.7 | 25.1 | 5.7 |
| heart | 0.6 | 0.3 | 0.4 | 0.1 | 0.1 | 0.3 |
| lungs | 47.4 | 3.7 | 27.9 | 3.7 | 2.2 | 0.6 |

TABLE 2-continued

Biodistribution of $^{99m}$Tc-peptide of Example 1 in normal Swiss-Webster mice at selected times after injection. All values are the mean ± standard deviation. n = 6 for all data points.

| ORGAN | % INJECTED DOSE/ORGAN | | |
|---|---|---|---|
| | 10 MINUTES | 30 MINUTES | 120 MINUTES |
| bone | 2.7 0.5 | 2.7 0.2 | 2.7 0.6 |
| muscle | 7.0 2.5 | 5.9 0.7 | 3.7 0.8 |
| thyroid | 0.1 0.0 | 0.1 0.0 | 0.1 0.0 |

Some studies involved pre-incubation of the $^{99m}$Tc-peptide in whole blood prior to injection and determination of biodistribution. In these studies, whole human blood was obtained from a healthy adult male donor and collected into Vacutainer tubes containing EDTA. After mixing to insure proper dissolution of the EDTA, approximately 2.5 ml of the whole blood was removed and mixed with 0.25 ml of $^{99m}$Tc-peptide. The mixture was allowed to incubate 30 minutes at room temperature. After 30 minutes, aliquots of 0.1 ml were injected into the tail vein of the mice. The amount of radioactivity in the circulation for $^{99m}$Tc-peptide of Example 1 pre-incubated in whole blood was higher than in animals receiving $^{99m}$Tc-peptide without incubation in blood. With incubation of $^{99m}$Tc-peptide in whole blood prior to injection, significantly decreased lung uptake was noted (Table 3).

TABLE 3

Biodistribution in normal Swiss-Webster mice of $^{99m}$Tc-peptide of Example 1 after a 30 minute pre-incubation in whole blood. All values are the mean ± standard deviation. n = 6 for all data points.

| ORGAN | % INJECTED DOSE/ORGAN | |
|---|---|---|
| | 10 MINUTES | 30 MINUTES |
| blood | 19.0 ± 1.6 | 10.8 ± 0.9 |
| stomach | 0.6 0.1 | 0.4 0.1 |
| sm. intestine | 2.8 0.2 | 4.2 0.8 |
| appendix | 0.2 0.1 | 0.1 0.0 |
| lg. intestine | 0.4 0.1 | 0.3 0.0 |
| liver | 21.8 1.0 | 16.9 0.6 |
| spleen | 1.0 0.1 | 1.2 0.2 |
| kidneys | 8.1 0.9 | 8.4 0.9 |
| heart | 0.6 0.2 | 0.4 0.1 |
| lungs | 5.1 0.9 | 3.9 0.3 |
| bone | 4.6 0.6 | 4.3 0.6 |
| muscle | 10.5 1.0 | 6.6 1.4 |
| thyroid | 0.1 0.1 | 0.1 0.0 |

The clearance rates of the $^{99m}$Tc-peptide of Example 1 was evaluated in adult female Fischer 344 rats at 2 hours after injection. Each experimental group was composed of three animals. Each animal was anesthetized with ketamine and the bile duct and bladder were cannulated. Blood was collected over various periods of time from the jugular vein. The $^{99m}$Tc-peptide cleared very rapidly from the plasma of rats, with a clearance rate of 2.4 ml/minute. At two hours, 10.8±4.9 of the injected dose had cleared through urine, while bile clearance at the same time point was 0.9±0.3%.

EXAMPLE 5

DOSE RESPONSE ON LUNG LOCALIZATION

The effect of the dose of $^{99m}$Tc-peptide of Example 1 on lung localization was evaluated. Localization in the lung was found in all injection doses used (0.05, 0.5, and 5 μg) at both 10 and 30 minutes post injection. Similar amounts of radioactivity were found in the lungs regardless of the amount injected at 10 minutes post injection (110.6%, 111.9%, and 144.4% I.D./gram of lung tissue for 0.05, 0.5, and 5 μg, respectively). At 30 minutes post injection a more pronounced effect of dose was noted, with more radioactivity retained in the lung with a larger injection dose (48.8%, 68.1%, and 91.9% I.D./gram of lung tissue for 0.05, 0.5, and 5 μg, respectively).

EXAMPLE 6

EXAMINATION FOR PARTICULATE IMPACTION

Certain experiments were conducted to determine if high lung uptake resulted from the preparation of Example 1 forming a particle which impacts in the lung. No particles were visible when freshly radiolabeled $^{99m}$Tc-peptide of Example 1 was examined under a phase contrast microscope, and $^{99m}$Tc-peptide of Example 1 filtered through a submicron filter (0.2 micron pore size) still localized to the lungs. Additionally, when $^{99m}$Tc-peptide of Example 1 was injected into the peritoneal cavity (to sequester potential colloid), localization to the lung was still found. In these experiments, the lung-heart ratio of $^{99m}$Tc-peptide of Example 1 was elevated (3:1) at 15 minutes after i.p. injection, and increased so that by 60 minutes post injection the ratio was 9:1. At 120 minutes the ratio had decreased, but was still nearly 6:1.

EXAMPLE 7

BIODISTRIBUTION IN MELANOMA TUMOR BEARING MICE

Biodistribution studies involving nude mice bearing melanoma tumors in the lung were conducted. Aliquots of B-16 melanoma cells were injected (50,000 cells in 0.1 ml serum-free RPMI medium) into the tail vein of adult nude mice and were used in studies approximately 3 weeks after inoculation. Paired studies were done using nude mice receiving sham injections of saline without cells.

The biodistribution of $^{99m}$Tc-peptide of Example 1 was markedly altered in animals with tumors in the lung compared to those without tumors in the lung. In these studies, five tumored and five control animals were used for each time point, and results are ± the standard deviation. In tumored animals, the amount of lung uptake (% injected dose) was increased compared to controls at all time points examined, so that with tumored animals lung uptake was 38.3±4.0 %, 28.1±3.6 % and 3.9±1.2 % at 10, 30, and 120 minutes post-injection, while with control nude mice at the same time points, the lung uptake was 19.0±2.7 %, 11.9±2.9 % and 1.6±0.4 %, respectively.

EXAMPLE 8

BIODISTRIBUTION IN EMPHYSEMA MODEL MICE

Biodistribution was also studied in a lung disease model which used tight-skin mice with genetic emphysema. The tight-skin (Tsk) mouse is a Genetic mutant caused by a dominant gene deficiency of serum anti-elastase. Heterozygous (Tsk/+) animals show multiple skin connective tissue abnormalities resembling scleroderma as well as an increased growth of cartilage, bone, and small tendons with hyperplasia of the tendon sheaths. The Tsk trait is associated with progressive pulmonary emphysema and development of right ventricular hypertrophy, as well as with lung collagen changes. These mice, as well as Genetic control mice (pallid), were obtained from The Jackson Laboratory (Bar Harbor, Me.).

The relative localization of $^{99m}$Tc-peptide of Example 1 at all time points examined (10, 30, and 120 minutes post-injection), was decreased in the lungs of animals with emphysema relative to paired control animals.

TABLE 4

Biodistribution of $^{99m}$Tc-peptide of Example 1 in tight-skin (Tsk) mice and genetic control mice at selected times after injection. All values are the mean ± standard deviation. n = 4 for all time points except 10 minutes, where n = 3.

| MICE | % INJECTED DOSE/LUNG | | |
|---|---|---|---|
| | 10 MINUTES | 30 MINUTES | 120 MINUTES |
| Tight-skin (Tsk) Mice | 10.4 ± 2.1 | 8.8 ± 0.6 | 8.5 ± 0.8 |
| Genetic Control Mice | 15.8 ± 2.7 | 11.9 ± 0.7 | 12.8 ± 2.7 |

In a degenerative lung disease like emphysema the total number of receptors would be expected to decrease, due to loss of lung mass. In such a case, the amount of localization of $^{99m}$Tc-peptide in the lungs would decrease relative to the /lodalization found in paired genetic control animals. The observations made correlate with this hypothesis.

All of the foregoing are merely illustrative, and other equivalent embodiments are possible and contemplated. The preceding examples can be repeated with similar success by substituting the generically or specifically described reactants and/or operating conditions of this invention for those used in the preceding examples.

Although the invention has been described in detail with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, publications and other references cited above are hereby incorporated by reference.

What is claimed is:

1. A method of performing a diagnostic procedure in a patient, comprising the steps of:
    a) preparing a medically useful metal ion-labeled peptide comprising a peptide sequence comprising the sequence IKVAV (SEQ. ID NO. 1) and a medically useful metal ion; and
    b) administering an effective amount of the medically useful metal ion-labeled peptide to the patient.

2. The method of claim 1, wherein the diagnostic procedure further comprises imaging by metal ion detection means.

3. The method of claim 2, wherein the diagnostic procedure comprises diagnosis and detection of pathologies and disease of the lung.

4. The method of claim 3, wherein the diagnosis and detection of pathologies and disease of the lung comprises diagnosis and detection of at least one condition selected from the group consisting of chronic obstructive pulmonary diseases, primary lung carcinomas and metastatic cancers in the lung.

5. The method of claim 4, wherein the diagnosis and detection of chronic obstructive pulmonary diseases comprises diagnosis and detection of at least one condition selected from the group consisting of emphysema and fibrosis.

6. The method of claim 1, wherein the peptide comprising the sequence IKVAV (SEQ. ID NO. 1) in step a) is a peptide comprising the sequence CSRARKQAASIKVAVSADR (SEQ. ID NO. 2).

7. The method of claim 1, wherein the medically useful metal ion-labeled peptide further comprises a chelating agent, whereby the medically useful metal ion is bound to the peptide via the chelating agent.

8. The method of claim 7 wherein the chelating agent is a bifunctional agent.

9. The method of claim 1 wherein the administration is parenteral, and comprises at least one method selected from the group consisting of intradermal, subcutaneous, intramuscular, intraperitoneal and intravenous injection.

10. The method of claim 1, wherein the medically useful metal ion-labeled peptide comprises a metal ion-binding domain, such that the medically useful metal ion-labeled peptide comprises the sequence IKVAV (SEQ. ID NO. 1) and a metal ion-binding domain, whereby the linked medically useful metal ion is bound to the peptide via the metal ion-binding domain.

11. The method of claim 10 wherein the peptide combination comprising the sequence IKVAV (SEQ. ID NO. 1) and a metal ion-binding domain is selected from the group consisting of $(R_1)-[Y_1]_n-(R_2)$, $(R_1)-[Y_1-(R_2)-Y_1]_n-(R_3)$, and $(R_1)-[Y_1-(R_2)-Y_2]_n-(R_3)$ wherein the metal ion-binding domain comprises a member selected from the group consisting of $[Y_1]_n$, $[Y_1-(R_2)-Y_1]_n$ and $[Y_1-(R_2)-Y_2]_n$ wherein n is a number between 1 and about 6, and $Y_1$ and $Y_2$ are amino acids comprising at least one element selected from the group consisting of sulfur, nitrogen and oxygen which is available or can be made available for binding to metal ions;

the peptide sequence IKVAV (SEQ. ID NO. 1) is present in at least one member selected from the group consisting of $R_1$, $R_2$ and $R_3$ and further comprises an amino acid sequence containing from 5 to about 20 amino acids; and those portions of $R_1$, $R_2$ and $R_3$ not comprising the peptide sequence IKVAV (SEQ. ID NO. 1) each comprise an amino acid sequence containing from 0 to about 20 amino acids.

12. The method of claim 10 wherein the metal ion-binding domain comprises at least one amino acid sequence selected from the group consisting of cystsine, cystins, histidine, penicillamine, deacylated methionine, lysine, arginine, aspartic acid, glutamic acid and tyrosine.

13. The method of claim 12 wherein the metal ion-binding domain comprises at least one member selected from the group consisting of $[Cys]_n$, $[Cys-(R_2)-Cys]_n$, $[Cys-(R_2)-Pen]_n$, $[His-(R_2)-Cys]_n$, $[His-(R_2)-Pen]_n$, $[His]_n$, and $([His-(R_2)-His]_n$ wherein n is a number between 1 and about 6; and $R_2$ is an amino acid sequence containing from 1 to about 20 amino acids.

14. The method of claim 2 wherein said metal ion detection means comprises imaging with at least one method selected from the group consisting of gamma scintigraphy, specific photon emission computerized tomography, positron emission tomography and magnetic resonance imaging.

15. The method of claim 1 wherein the medically useful metal ion comprises at least one ionic element selected from the group consisting of iron, cobalt, nickel, copper, zinc, arsenic, selenium, molybdenum, technetium, ruthenium, palladium, silver, cadmium, indium, antimony, rhenium, osmium, iridium, platinum, gold, mercury, thallium, lead, bismuth, polonium and astatine.

16. The method of claim 1 wherein the medically useful metal ion comprises at least one property selected from the group consisting of radioactivity, parmagnetism and superparamagnetism.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 1:

Ile Lys Val Ala Val
        1                     5

( 2 ) INFORMATION FOR SEQ ID NO:2:

( i ) SEQUENCE CHARACTERISTICS:
        ( A ) LENGTH: 19 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No (x i) SEQUENCE DESCRIPTION: SEQ ID NO: 2:

```
Cys Ser Arg Ala Arg Lys Gln Ala Ala Ser Ile Lys Val Ala
1               5                   10

Val Ser Ala Asp Arg
15
```

(2) INFORMATION FOR SEQ ID NO:3:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: Peptide (iii) HYPOTHETICAL: No (iv) ANTI-SENSE: No (xi) SEQUENCE DESCRIPTION: SEQ ID NO: 3:

```
Arg Lys Gln Ala Ala Ser Ile Lys Val Ala Val
1               5                   10
```

(2) INFORMATION FOR SEQ ID NO:4:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: Peptide (iii) HYPOTHETICAL: No (iv) ANTI-SENSE: No (xi) SEQUENCE DESCRIPTION: SEQ ID NO: 4:

```
Tyr Ile Gly Ser Arg
1               5
```